US006019981A

United States Patent [19]
Klesius et al.

[11] Patent Number: 6,019,981
[45] Date of Patent: Feb. 1, 2000

[54] **MODIFIED LIVE *EDWARDSIELLA ICTALURI* AGAINST ENTERIC SEPTICEMIA IN CHANNEL CATFISH**

[75] Inventors: Phillip H. Klesius, Auburn; Craig A. Shoemaker, Notasulga, both of Ala.

[73] Assignee: The United States of America as represented by the Secretary of Agriculture, Washington, D.C.

[21] Appl. No.: 09/053,261

[22] Filed: Mar. 6, 1998

[51] Int. Cl.[7] .......................... A61K 39/02; A61K 39/00; A01N 63/00

[52] U.S. Cl. .................. 424/234.1; 424/93.2; 424/93.48; 424/93.4; 424/235.1; 424/200.1; 424/184.1; 424/93.1; 424/827

[58] Field of Search ............................. 424/234.1, 235.1, 424/827, 184.1, 93.1, 93.2, 93.4, 93.48; 435/243

[56] References Cited

U.S. PATENT DOCUMENTS

| | | | |
|---|---|---|---|
| 5,151,023 | 9/1992 | Kuzuhara et al. | 424/89 |
| 5,284,653 | 2/1994 | Wolf-Watz et al. | 424/92 |
| 5,536,658 | 7/1996 | Shotts et al. | 435/252.3 |
| 5,747,309 | 5/1998 | Allan et al. | 435/172.3 |

FOREIGN PATENT DOCUMENTS

| | | |
|---|---|---|
| WO 98/46725 | 10/1998 | WIPO . |

OTHER PUBLICATIONS

Klesius et al. Ann.Rev. Fish Dis. (ed) Faisal et al. Pergamon Press, New York, pp. 325–338, 1992.

Schurig et al. Veter. Microbiol. 28: 171–188, abstract, 1991.

Linde et al. Vaccine 9: 101–105, abstract, 1991.

Linde et al. Vaccine 11: 197–200, abstract, 1993.

Linde et al. Vaccine 8: 25–29, abstract, 1990.

Thune et al. In: Meeting of the Fish Health Section, American Fisheries Society, Madison, Wisconsin, USA Aug. 6–9, 1996.

Hawke et al. Inter. J. System. Bacteriol. 31: 396–400, abstract, 1981.

Meyer et al. Appl. Microbiol. 25: 155–156, 1973.

P Klesius et al. Heterologous isolates challenge of channel catfish immune to *Edwardsiella ictaluri*. In: R. Gudding et al. (Ed), Developmenta in Biological Standardization, vol. 90. Fish Vaccinology, Meeting, Oslo, Norway, Jun. 5–7, 1996. xiv+484p. S. Ka, 1997.

RL Thune et al. J. World Aquacul. Soc. 28(2):193–201, 1997.

JW Tyler et al. Am. J. Vet. Res. 55(9): 1256–1260, 1994.

*Primary Examiner*—Christopher L. Chin
*Assistant Examiner*—S. Devi
*Attorney, Agent, or Firm*—M. Howard Silverstein; Joseph A. Lipovsky; John D. Fado

[57] ABSTRACT

Safe and effective live vaccines against enteric septicemia of catfish (ESC) were created through the induction of rifampicin resistance in native *E. ictaluri* isolates; these including rifampicin-resistant strain (RE-33) of *Edwardsiella ictaluri* originally isolated from the walking catfish *Clarius batrachus* from Thailand. Single immersion exposure of catfish fry stimulated strong acquired immunity against many isolates of *E. ictaluri* without the need for booster immunization.

13 Claims, No Drawings

MODIFIED LIVE *EDWARDSIELLA ICTALURI* AGAINST ENTERIC SEPTICEMIA IN CHANNEL CATFISH

BACKGROUND OF THE INVENTION

1. Field of the Invention

*Edwardsiella ictaluri*, the causative agent of enteric septicemia of catfish (ESC), is a Gram-negative bacterium that is highly infectious for the channel catfish *Ictalurus punctatus*. This pathogen has been isolated from channel catfish in most areas of the United States where this species is cultured and from walking catfish in Thailand [Kasornchandra et al., J. Fish Dis. 10:137–138(1987). Losses in fingerlings to market-size fish account for about 50% of the total disease losses to catfish producers. Formalin-killed bacterial vaccines have not been successful due to their provoking only a humoral response. This is due to *Edwardsiella ictaluri* being an intracellular pathogen, with acquired immunity in fish surviving ESC being more cellular than humoral.

This invention relates to a novel vaccine against ESC which does in fact provide superior protection over existing commercial vaccines due to its ability to stimulate cellular-immunity and protection.

2. Description of the Prior Art

It has been estimated that ESC is responsible for annual losses of 20 to 30 million dollars in the catfish industry. Control of *E. ictaluri* has been attempted by feeding antibiotic medicated feed. This expensive practice has been ineffective because sick fish do not eat and antibiotic resistance to oxytetracycline and ormethoprim-sulfamethoxine, the approved drugs for use on food fish, has been observed.

Based on the success of disease control by bacterin immunization of salmonids, bacterins were developed against ESC. An *E. ictaluri* bacterin (ESC vaccine, ALPHARMA, formerly BIOMED, Inc., 1720-130th Ave. N.W., Bellevue, Wash., USA) was produced and marketed with a provisional license for immersion vaccination of channel catfish against ESC. An oral *E. ictaluri* bacterin (Escogen, Aqua Health, Ltd., Charlottetown, PEI, Canada) was produced, marketed and licensed for oral vaccination of channel catfish against ESC. Thune et al. [*J. Appl. Aquaculture* 3, 11–23 (1994)] teach that vaccination of channel catfish (*Ictalurus punctatus*) with *E. ictaluri* bacterins has not resulted in acquired immunity of long duration. Nusbaum and Morrison [*J. Aquat. Animal Health* 8, 146–149 (1996)] also demonstrated that killed *E. ictaluri* was not entering the fish and suggested that this affected vaccine efficacy. *Edwardsiella ictaluri* has been described as a facultative intracellular pathogen of channel catfish [Miyazaki et al.; *J. Fish Dis.* 8, 389–392 (1985)]. Because of the nature of *E. ictaluri* as an intracellular pathogen, it is not surprising that killed vaccines have not been successful. Strictly controlled live vaccination of channel catfish with low concentrations of unmodified isolates of *E. ictaluri* by bath immersion was found to stimulate protective immunity, specific antibodies by Klesius et al. [Journal of Aquatic Animal Health 7, 205–210 (1995)]. Protective immunity to *B. abortus* in cattle was demonstrated by Montaraz et al. [*Infect. Immun.* 53, 245–251 (1986)] and Schurig et al. [*Vet. Micro.* 28, 171–188 (1991)] using vaccines based on modified live rifampicin-resistant Brucella species.

SUMMARY OF THE INVENTION

We have now discovered a means for the creation of novel live vaccines that are safe and effective for the control of ESC in catfish. The vaccines comprise one or more rifampicin (3-[4-methylpiperazinyliminomethyl]rifamycin SV) (Sigma Chemical Company, St. Louis, Mo.) resistant mutant isolates of *E. ictaluri*, created by multiple passaging of native isolates on increasing concentrations of rifampicin. These vaccines are effective in providing long lasting acquired immunity in channel catfish to ESC.

In accordance with this discovery, it is an object of the invention to provide a novel, highly protective, live vaccine against ESC in catfish.

It is also an object of this invention to provide both monovalent and polyvalent vaccines against ESC that are more efficacious than those presently in commercial use.

It is another object to provide an attenuated *Edwardsiella ictaluri* vaccine that is safe and provides long lasting acquired immunity in channel catfish to enteric septicemia of catfish.

It is a further object of this invention to improve the viability and productivity of catfish, and to reduce economic losses in the catfish industry caused by ESC.

Other objects and advantages of the invention will become readily apparent from the ensuing description.

Deposit of Biological Material

Rifampicin-resistant attenuated *Edwardsiella ictaluri* isolate EILO RE-33, was deposited on Nov. 26, 1997, under the provisions of the Budapest Treaty with the American Type Culture Collection located at 10801 University Boulevard, Manassas, Va. 20110-2209, and has been assigned Accession No. ATCC 202058.

Rifampicin-resistant attenuated *Edwardsiella ictaluri* isolates RA-75-34, RS-629-34, and RS-694-34 were deposited on Jan. 12, 1998 under the provisions of the Budapest Treaty in the Agricultural Research Service Culture Collection located at 1815 North University Street, Peoria, Ill. 61604, and have been assigned Deposit No.'s B-21909, B-21910, and B-21911 respectively.

DETAILED DESCRIPTION OF THE INVENTION

"Vaccine" is defined herein in its broad sense to refer to any type of biological agent in an administratable form capable of stimulating a protective immune response in an animal inoculated with the vaccine. For purposes of this invention, the vaccine may comprise one or more live attenuated isolates of *Edwardsiella ictaluri* having the characteristic of rifampicin-resistance.

The starting material for use in preparing the vaccines of the invention may be any isolate of *Edwardsiella ictaluri*. Serial passage of the isolate of *Edwardsiella ictaluri* over increasing concentrations of rifampicin produces strains with an attenuated pathogenicity efficacious for the preparation of live vaccines. The methodology for attenuation by serial passage is well known and documented in the art as exemplified by Schurig et al. [*Vet. Micro.* 28, 171–188 (1991)], hereby incorporated by reference, who created vaccines based on modified live rifampicin-resistant Brucella species.

The term "revertant" is intended to refer to a subculture of an attenuated bacterium, the subculture being characterized by increased virulence and increased in vivo replication as compared to the attenuated form. The term is used herein generically to encompass both true revertants and apparent revertants, the latter being derived from an existing bacterial population.

The starting material for use in preparing the vaccines of the invention is any attenuated *Edwardsiella ictaluri* bacterium such as the EILO RE-33 bacterium reported supra. The attenuation achieved by high-level serial passage in culture on increasing concentrations of rifampicin virtually eliminates the pathogenicity of the bacterium toward channel catfish. The native strain of *Edwardsiella ictaluri* should be passaged a sufficient number of times such that in its new attenuated form it no longer possesses the ability of causing the disease state known as enteric septicemia in catfish. The efficacy of the monovalent vaccine against challenge by certain strains of native *Edwardsiella ictaluri* is however not universal. The vaccinal efficacy can be enhanced by combining multiple attenuated strains of *Edwardsiella ictaluri* into bivalent or polyvalent vaccines.

Vaccination, while being accomplishable by injection or through oral ingestion, is most efficiently done by means of aqueous immersion. The bacterial agent is prepared for administration by formulation in an effective immunization dosage with an acceptable carrier or diluent, such as water. The expression "effective immunization dosage" is defined as being that amount which will induce immunity in a catfish against challenge by a virulent strain of ESC. Immunity is considered as having been induced in a population of catfish when the level of protection for the population is significantly higher than that of an unvaccinated control group. One measure of the level of protection is the protective index (PI), which is calculated as the ESC in unvaccinated, ESC bacteria challenged controls minus the ESC in vaccinated, ESC bacteria challenged groups, and the difference divided by the percent ESC in unvaccinated, ESC bacteria challenged controls, with the result multiplied by 100. Typically, vaccination is carried out by exposing channel catfish by immersion in water containing about $1 \times 10^5$ CFU/ml of attenuated *Edwardsiella ictaluri* for two minutes at a density of about 50 fish/L and a temperature of about 25° C. These parameters may be varied as desired such that a sufficient level of vaccination is acquired without induction of excessive loss. Useable concentrations of *Edwardsiella ictaluri* are considered to range from about $5 \times 10^4$ to about $1 \times 10^8$ CFU/ml of immersion medium. Useable vaccination times are seen to range from about 1 minute to about 60 minutes, preferably from about 2 minutes to about 10 minutes. Temperature of the inoculation media may range within the physiologically acceptable limits of catfish, preferably from about 18° C. to about 28° C., most preferably from about 22° C. to about 26° C. Concentrations of fish treated in the inoculation medium typically range from about 50 to about 100 fish/L, but, in the alternative, be determined on a weight basis and range from about 0.5 to about 2.5 kg/L. The vaccine can be effectively administered anytime after the catfish attains immunocompetence, which is at about the second day post-hatch.

Appropriate adjuvants as known in the art may also be included in the vaccine formulation. In many cases, the vaccinal efficacy can be enhanced by combining the different strains of attenuated *Edwardsiella ictaluri* into bivalent or polyvalent vaccines.

The following examples are intended only to further illustrate the invention and are not intended to limit the scope of the invention which is defined by the claims.

EXAMPLE 1

The procedure used to produce the RE-33 vaccine was modified from that described in Shurig et al. (1991; Vet Micro 28, 171–188), hereby incorporated by reference, by using a lower initial concentration of rifampicin and ending at 320 µg/ml instead of 200 µg/ml and by omitting the penicillin step.

Process of Developing Resistant Mutants of *Edwardsiella ictaluri*

Brain heart infusion agar plates for the cultivation of *Edwardsiella ictaluri* were made according to the procedure of Difco (Difco, Inc., Detroit, Mich.). 37 g of brain heart infusion media and 17 g of agar are added to one liter of distilled water. The media and agar were heated until dissolution. The media was then autoclaved at 121–124° C. for 15 minutes, the media was then poured into sterile petri dishes (15 ml per dish) and allowed to solidify before refrigeration.

Native isolates of *Edwardsiella ictaluri* were obtained from sick catfish or previously obtained lyophilized stocks. Isolates of *E. ictaluri* were then identified by standard biochemical tests as set forth in *Bergey's Manual of Determinative Bacteriology* prior to use in rifampicin resistant *E. ictaluri*. After identification, the process of forming rifampicin resistant isolates of *Edwardsiella ictaluri* was begun. Rifampicin supplemented brain heart infusion agar plates were prepared as follows: Brain heart infusion agar was made as described above and sterilized at 121–124° C. for 15 minutes. After sterilization, the correct amount of rifampicin was added to the media prior to its solidification and 15 ml of the resulting mixture was poured into separate petri dishes and allowed to solidify prior to refrigerated storage. Initial cultures of the native isolates of *Edwardsiella ictaluri* were grown on brain heart infusion agar plates which were incubated at 20–25° C. for 24–48 hours or until 1–2 mm translucent colonies were observed. A single *E. ictaluri* colony was then picked with a sterile inoculating loop and streaked onto a rifampicin supplemented brain heart infusion agar plate containing the correct concentration of the antibiotic. For the initial passage, rifampicin was present in the brain heart infusion agar at a concentration of 5 µg/ml. The rifampicin supplemented brain heart infusion agar which was streaked with the aforementioned native isolate of *E. ictaluri* was then incubated for 24–48 hours at 20–25° C. and observed for bacterial growth. Single colonies of *E. ictaluri* which grew on the rifampicin supplemented media were then picked and placed onto the next concentration of rifampicin (10 µg/ml) brain heart infusion agar plates. If growth occurs, a single colony is harvested and placed on an agar media containing the next higher concentration of rifampicin (20 µg/ml). If the harvested colony failed to grow, it was repeatedly passed on a media containing the last concentration of rifampicin at which growth successfully occurred, before being placed on the next higher concentration of rifampicin containing media. This process was repeated until a colony capable of growing on a media containing a rifampicin concentration of 320 µg/ml was created.

*Edwardsiella ictaluri* isolate EILO was passaged on increasing concentrations of rifampicin (3-[4-methylpiperazinyl-iminomethyl]rifamycin SV) (Sigma Chemical Company, St. Louis, Mo.) supplemented brain heart infusion (BHI) agar to a final concentration of 320 µg/ml rifampicin for 33 passages. The resultant mutant, designated RE-33, is differentiated from the parent microorganism because it can survive and reproduce without negative effect on a media containing 320 µg/ml rifampicin. Biochemical characteristics of the *E. ictaluri* EILO RE-33 are identical to *E. ictaluri* as described in *Bergey's Manual of Determinative Bacteriology* (Holt et al., 1994), herein incorporated by reference.

EXAMPLE 2

Lipopolysaccharide (LPS) was extracted as described by Schurig et al. (1991, ibid.). Bacterial growth from a 250 ml BHI broth culture of both the parent EILO and RE-33 was harvested by centrifugation. The cell pellet was then suspended in 25 ml of 10 mM Tris, pH 8.0 and bacteria were killed by addition of an equal volume of acetone, and stirred overnight. Cells were centrifuged at 13,000×g for 5 minutes at 4° C. and then washed with 100 ml of sterile distilled water. The bacteria were then resuspended in 45 ml of sterile distilled water and then 55 ml of phenol was added (incubated at 68° C. for 40 minutes). The mixture was then centrifuged at 17,000×g at 4° C. for 10 minutes. The phenol layer was removed and the process repeated three times. The phenol phases were pooled and washed with hot distilled water (about 66° C.), and centrifuged at 17,000×g at 4° C. for 10 minutes and the resulting pellet harvested in 10 ml sterile distilled water. This was then frozen at −70° C. and subsequently lyophilized. Samples of phenol extracted LPS from *E. ictaluri* EILO and RE-33 were treated as described by Schurig et al. (1991; ibid.) prior to electrophoresis. SDS-PAGE electrophoresis was then carried out using the Phast system (Pharmatech-Biotech, Uppsala, Sweden) with 10–15% gradient gels. The gels were then silver stained to examine for the presence or absence of the O-side chain of LPS. Silver stained SDS-PAGE profiles of lipopolysaccharide extracted from *E. ictaluri* RE-33 indicated that the O-chain was not present as compared to the parent *E. ictaluri* EILO lipopolysaccharide.

EXAMPLE 3

A total of 16,460 channel catfish, blue catfish (*Ictalurus furcatus*), and blue catfish x channel catfish free of *E. ictaluri* were vaccinated by immersion with about 1×10⁵ CFU/ml RE-33 vaccine for two minutes at a density of about 50 fish/L in 24–26° C. water. Immunized fish were kept in 1500 L fiberglass tanks supplied with recirculating or well water at 18 or 26° C. with a flow rate of 0.5 L/minute. Fish were fed daily a commercial catfish ration at 4% of their body weight. Fish utilized in the experiment ranged in size from about 10 grams to about 50 grams and ranged from about 3 to about 9 months of age. Fish were observed daily for mortalities, abnormal behavior, and to monitor for any signs of ESC. In the experiment, comprising 10 separate runs lasting from 14 to 120 days post vaccination, no signs of ESC or mortality were seen in any of the fish. The results are presented below in Table I.

TABLE I

SAFETY OF VACCINE DOSE OF *EDWARDSIELLA ICTALURI* RE-33 IN CHANNEL CATFISH, BLUE CATFISH AND BLUE CATFISH X CHANNEL CATFISH VACCINATES

| Experiment | Date | Species or Strains | Numbers Vaccinated | Number Alive/Day Post Vaccination (DPV) | Signs of ECS or Mortality |
|---|---|---|---|---|---|
| 1 | 7/96 | Marion | 60 | 60/14 | None |
| 2 | 10/96 | USDA | 125 | 125/14 | None |
| 3 | 10/96 | USDA | 1050 | 1050/60 | None |
| 4 | 11/96 | USDA | 525 | 525/30 | None |
| 5 | 12/96 | USDA | 1100 | 1100/120 | None |
| 6 | 1/97 | USDA | 1100 | 1100/90 | None |
| 7 | 5/97 | USDA | 3500 | 3500/90 | None |
| 8 | 5/97 | Norris X USDA | 3000 | 3000/90 | None |
| 9 | 5/97 | Blue X USDA | 3000 | 3000/90 | None |
| 10 | 5/97 | Blue | 3000 | 3000/90 | None |
| | | Total | 16460 | 16460 | None |

EXAMPLE 4

Channel catfish (125 USDA and 60 Marion strain) were vaccinated following the protocols of EXAMPLE 3 at 200 times the normal vaccine dose (2×10⁷/ml) for 30 times longer exposure (1 hour) to determine the safety of the vaccine. Results of experimental challenge are presented as relative percent survival (RPS) as described by Amend (1981; Dev. Biol. Stand. 49, 447–454), herein incorporated by reference. RPS is calculated according to the following formula:

$$RPS = 1 - \frac{\% \text{ vaccinate mortality}}{\% \text{ control mortality}} \times 100$$

A positive effect by vaccination is a RPS greater than 50%.

At fourteen days post vaccination (DPV) the relative percent survival was 94.7%. No fish died after the vaccination. In this study, mortality in an equivalent group of 125 untreated controls was 92%.

EXAMPLE 5

Twenty catfish (blue x channel catfish) were injected intraperitoneally (IP) with 50 μl of a 24 hour culture of RE-33 which was isolated from channel catfish after vaccination. Reversion to virulence did not occur in any of the twenty fish tested. No mortality or signs of ESC were observed in the fish for 35 days after injection.

EXAMPLE 6

Five serial passages of *E. ictaluri* RE-33 were conducted in five groups of ten channel catfish to examine reversion to virulence. *E. ictaluri* RE-33 was obtained from a vaccinated channel catfish and grown in BHI broth for 24 hours before use. The first group of ten fish was vaccinated at the normal dose and time. Two to three days following vaccination, two to three fish were euthanized and cultured for *E. ictaluri* RE-33. After a pure culture was obtained, the process was repeated five times. Fifty channel catfish were immersed in 2 ml/L RE-33 culture which had been streaked on 320 μg/ml rifampicin supplemented BHI agar plates to non-rifampicin supplemented plates for 16 passages. Reversion to virulence did not occur. The fish used in this experiment were held in the laboratory without signs of ESC or adverse behavior for at least 20 days. *Edwardsiella ictaluri* RE-33 was not isolated from five fish sampled 12 days after injection. No mortality or signs of ESC were observed for 35 days in the 50 fish utilized in the test.

EXAMPLE 7

Induction of protective immunity by *E. ictaluri* RE-33 was examined in relation to 12 different *E. ictaluri* isolates obtained from diseased channel catfish throughout the Southeast and the parent isolate from Thailand. These are listed below in Table II.

were challenged with the 13 *E. ictaluri* isolates at concentrations of $2 \times 10^7$/ml for one hour. Controls were immersed in brain heart infusion broth only. Relative percent survivals were greater than or equal to 50% at 14 DPV (days post vaccination) for 8 of the 13 isolates tested (see Table III).

TABLE III

PROTECTION AGAINST ENTERIC SEPTICEMIA OF CATFISH (ESC) AFTER IMMERSION VACCINATION[1] OF CHANNEL CATFISH WITH *EDWARDSIELLA ICTALURI* RE-33 VACCINE

| Experiment | Days Post Vaccination (DPV) | Number of Fish Vaccinated | *E. ictaluri* Challenge[2] Isolate | Relative Percent Survival (RPS)[3] | Percent Mortality in Controls |
|---|---|---|---|---|---|
| 1 | 14 | 60 | EILO[4] | 51.7 | 100.0 |
| 2 | 14 | 60 | AL-93-75 | 98.3 | 100.0 |
| 3 | 14 | 125 | AL-93-75 | 96.6 | 94.6 |
| 4 | 14 | 60 | AL-93-75 | 96.8 | 94.4 |
| 5 | 84 | 60 | AL-93-75 | 93.9 | 26.4* |
| 6 | 105 | 60 | AL-93-75 | 78.9 | 79.3 |
| 7 | 14 | 60 | S94-873 | 54.0 | 68.3 |
| 8 | 14 | 60 | S94-1017 | 71.7 | 100.0 |
| 9 | 14 | 60 | S94-1051 | 50.0 | 100.0 |
| 10 | 14 | 60 | AL-96-25 | 50.4 | 96.7 |
| 11 | 14 | 60 | S94-827 | 47.0 | 96.7 |
| 12 | 14 | 60 | S94-1034 | 27.0 | 98.3 |
| 13 | 14 | 60 | ATCC-33202 | 6.7 | 100.0 |
| 14 | 14 | 125 | AL-95-58 | 78.4 | 40.8* |
| 15 | 14 | 125 | S94-629 | 53.3 | 24.0* |
| 16 | 14 | 60 | S94-694 | 18.3 | 100.0 |
| 17 | 42 | 60 | S94-694 | 96.0 | 55.0* |
| 18 | 63 | 60 | S94-694 | 100.0 | 55.0* |
| 19 | 14 | 60 | S94-707 | 29.0 | 91.7 |
| 20 | 42 | 60 | S94-707 | 93.0 | 70.0 |
| Total | | 1395 | 13 isolates | Mean Protection = 64.6% | |

[1]Immersion vaccination with $1 \times 10^5$ *E. ictaluri* RE-33/ml for 2 minutes at a density of about 50 fish per L of water.
[2]Challenge with *E. ictaluri* isolates at 1 to $2 \times 10^7$/ml for 1 h described by Klesius and Sealey (1995) and Shoemaker and Klesius (1997).
[3]Relative percent survival (RPS) as determined by Amend (1981). RPS's $\leq 50\%$ are considered protection by vaccination (Amend, 1981).
[4]Parent of RE-33 vaccine strain.
*Data do not fit Amend's criteria of 60% mortality in controls.

TABLE II

*EDWARDSIELLA ICTALURI* ISOLATES USED IN EXPERIMENTS

| Isolate | Source | Location |
|---|---|---|
| AL-93-75 | channel catfish with ESC | Alabama |
| AL-95-58 | channel catfish with ESC | Alabama |
| AL-96-25 | channel catfish with ESC | Alabama |
| ATCC-33202 | American Type Culture Collection | Georgia |
| S94-629 | channel catfish with ESC | Mississippi |
| S94-649 | channel catfish with ESC | Mississippi |
| S94-707 | channel catfish with ESC | Mississippi |
| S94-827 | channel catfish with ESC | Mississippi |
| S94-873 | channel catfish with ESC | Mississippi |
| S94-1017 | channel catfish with ESC | Mississippi |
| S94-1051 | channel catfish with ESC | Mississippi |
| S94-1034 | channel catfish with ESC | Mississippi |
| EILO | walking catfish | Thailand |

Groups of either 60 or 125 channel catfish were vaccinated with *E. ictaluri* RE-33 according to the protocols set forth in Example 3. At 14 days post vaccination these fish By increasing the time after vaccination, protection was demonstrated as having been developed for two more of the isolates (S94-694 and S94-707).

EXAMPLE 8

Induction of protective immunity by *E. ictaluri* mutants RA-75-34, RS-629-34 and RS-694-34 were examined in relation to native *E. ictaluri* isolate AL-93-75 obtained from channel catfish in Alabama. Groups of 75 channel catfish were vaccinated with *E. ictaluri* mutants according to the protocols set forth in Example 3. At 14 days post vaccination these fish were challenged with the native *E. ictaluri* isolate at a concentration of $2 \times 10^7$/ml for one hour. Controls were immersed in brain heart infusion broth only. Relative percent survivals were greater than or equal to 50% at 14 DPV for vaccinated groups tested (see Table IV).

TABLE IV

EFFICACY OF RIFAMPICIN RESISTANT *E. ICTALURI* MUTANTS RA-75-34, RS-629-34 AND RS-694-34 IN CHANNEL CATFISH CHALLENGED WITH *E. ICTALURI*

| Treatment[1] | Number of Fish | Fish Dead Due to ESC after Challenge | Percent Mortality | Relative Percent Survival |
|---|---|---|---|---|
| Non-vaccinated controls | 75 | 35 | 46.67 | — |
| RA-75-34[2] | 75 | 2 | 2.67 | 94.3 |
| RS-629-34 | 75 | 7 | 9.33 | 80.0 |
| RS-694-34 | 75 | 17 | 22.67 | 51.4 |

[1]All fish were alive and free of signs of ESC for 21 days after vaccination.
[2]Fish were vaccinated at about $1 \times 10^7$ CFU / ml of each mutant.

It is understood that the foregoing detailed description is given merely by way of illustration and that modification and variations may be made therein without departing from the spirit and scope of the invention.

We claim:

1. An isolated attenuated strain of *Edwardsiella ictaluri* resistant to rifampicin and effective for eliciting an immune response in catfish which is protective against an infection by virulent strains of *Edwardsiella ictaluri* wherein said strain of *Edwardsiella ictaluri* is selected from the group consisting of ATCC 202058, B-21909, B-21910, and B21911.

2. A vaccine comprising: in an effective immunization dosage the attenuated strain of *Edwardsiella ictaluri* of claim 1 and a carrier.

3. The vaccine as described in claim 2 wherein said strain of *Edwardsiella ictaluri* is selected from the group consisting of ATCC 202058, B-21909, B-21910, and B-21911.

4. The vaccine as described in claim 2 wherein said carrier is water.

5. A method of providing protection for catfish against infection by virulent strains of *Edwardsiella ictaluri* comprising administering the composition of claim 2 to said catfish.

6. The method of claim 5 wherein said administration is by means of immersion in an aqueous system.

7. The method of claim 6 wherein said attenuated strain of *Edwardsiella ictaluri* is present in the immersion bath at a concentration greater than or equal to about $1\times10^5$/ml.

8. A polyvalent vaccine comprising: in an effective immunization dosage two or more attenuated strains of *Edwardsiella ictaluri* of claim 1 and a carrier.

9. The vaccine as described in claim 8 wherein said strains of *Edwardsiella ictaluri* are selected from the group consisting of ATCC 202058, B-21909, B-21910, and B-21911.

10. The vaccine as described in claim 8 wherein said carrier is water.

11. A method of providing protection for catfish against infection by virulent strains of *Edwardsiella ictaluri* comprising administering the composition of claim 8 to said catfish.

12. The method of claim 11 wherein said administration is by means of immersion in an aqueous system.

13. The method of claim 12 wherein each of said attenuated strains of *Edwardsiella ictaluri* are present in the immersion bath at a concentration greater than or equal to about $1\times10^5$/ml.

* * * * *